United States Patent [19]

Brunswick

[11] Patent Number: 4,716,892

[45] Date of Patent: Jan. 5, 1988

[54] ORTHOPEDIC SUPPORT APPARATUS WITH A BRACE-RECEIVING POCKET

[76] Inventor: Sumner Brunswick, 858 Huntington Ave., Boston, Mass. 02115

[21] Appl. No.: 944,461

[22] Filed: Dec. 19, 1986

[51] Int. Cl.⁴ .......................... A61F 5/04; A61F 5/02
[52] U.S. Cl. .................................. 128/77; 128/80 C; 128/68; 128/78; 128/87 R; 128/89 R
[58] Field of Search ................. 128/80 C, 71, 80 R, 128/87 R, 89 R, 78, 68, 26, 80 G, 87 A, 80 DB, 88

[56] References Cited

U.S. PATENT DOCUMENTS

| | | | |
|---|---|---|---|
| 2,206,404 | 7/1940 | Jones | 128/89 R |
| 3,779,550 | 12/1973 | Benoun et al. | 128/89 R |
| 3,906,943 | 9/1975 | Arluck | 128/87 R |
| 3,927,665 | 12/1975 | Wax | 128/78 |
| 4,040,632 | 8/1977 | Pawl | 128/77 |
| 4,183,098 | 1/1980 | Knowles, Jr. | 128/87 R |
| 4,366,812 | 1/1983 | Nuzzo | 128/77 |
| 4,384,571 | 5/1983 | Nuzzo et al. | 128/77 |
| 4,475,543 | 10/1984 | Brooks et al. | 128/78 |
| 4,572,167 | 2/1986 | Brunswick | 128/78 |

Primary Examiner—Charles A. Pearson
Assistant Examiner—Tonya Lamb
Attorney, Agent, or Firm—Lahive & Cockfield

[57] ABSTRACT

An improved orthopedic support device for body portions employs a pliable wrap which encircles the body portion and which has a pocket which receives a thermo-formable bracing element. A pocket-forming panel is secured only partially to the wrap for allowing the wrap to stretch more readily to mold with contours of the body portion. The invention further includes a process for fitting the device to a body portion with quick closure of the pocket for enhanced safety and for rapid molding of the bracing element to body contours.

7 Claims, 11 Drawing Figures

ORTHOPEDIC SUPPORT APPARATUS WITH A BRACE-RECEIVING POCKET

BACKGROUND

This invention relates to orthopedic support for small and/or irregularly contoured body portions such as the hands, forearms, wrists, knees, and feet. More particularly, the invention provides an orthopedic support apparatus and method for use with such body portions and which provides superior fit, support, and comfort.

U.S. Pat. No. 4,572,167 iscloses an orthopedic support device and method which employ a thermo-forming element which seats in a pocket of a belt-like wrap and which overcomes many shortcomings of prior orthopedic supports. The device and process of that patent are particularly useful for the back and other portions of the human trunk.

Orthopedic support for smaller body portions presents further problems. The contours of these body portions have relatively short radii of curvature and have protusions close to recesses to form irregular contours with bends and curves that reverse. One problem is the difficulty in configuring a lightweight, removable, replaceable, and reformable support device to fit such body portions with proper support and with a high degree of comfort. In addition, the application of an orthopedic device as described in the above-mentioned U.S. Pat. No. 4,572,167 to these relatively small and irregularly contoured body portions presents problems in terms of ensuring that the thermo-forming brace element is fully seated in the pocket of the support device.

It accordingly is an object of this invention to provide an improved orthopedic support device for protecting and supporting relatively small and irregularly contoured body portions. In particular, it is an object to provide a support device and method for body portions contoured with small and reversed radii of curvature and which is easily fitted to the subject.

A further object of the invention is to provide a structure for an orthopedic support device which employs a thermo-formable bracing element supported in a pliable wrap, and which forms that element readily to relatively small and irregularly contoured body portions.

Another object of the invention is to provide a process for fitting an orthopedic support device to such a body portion and which is quick and easy to perform, and which requires little manipulation of the patient.

Other objects and features of the invention will in part be obvious, and will in part be apparent from the drawing and the following description.

SUMMARY OF THE INVENTION

An improved orthopedic device according to the invention is easily fitted and molded to a boy portion that is relatively small and that is irregularly contoured, as with protrusions and recesses. The device also provides proper seating of a thermo-forming panel into a pocket of the device. In addition, an improved process according to the invention wraps an orthopedic support device about such a body portion to provide rapid, proper fit and molding of the device to the contours of the body portion with safety and with minimal manipulation of the body portion.

The invention includes an orthopedic support apparatus for a body portion which extends along an axis. Such body portions include hands, wrists, forearms, elbows, ankles, feet, arms, and knees, although features of the device may be used in supports for other body portions. The apparatus includes a pliable wrap with a re-entrant pocket for receiving a thermo-forming bracing element. The wrap includes a web element of pliable material with a selected contour and with selected maximal width and length dimensions. The web element is resiliently elastic at least along the length dimension.

The wrap has adjustable strap elements which extend along the length dimension for securing the web element at least partially encircling the body portion, about the axis, with the length dimension extending circumferentially about the body portion. In one preferred embodiment, the strap elements are of non-elastic material.

The strap elements preferably include two types of straps. A first type is adapted for initial securage of the wrap about the body portion. This allows for immediate molding of the heated bracing element to contours of the body portion. The second type of strap also secures the wrap about the body portion and can be readily deployed or redeployed for adjustment of the wrap. The first type of strap is selectively located for immediate securage of the wrap and thermo-forming of the bracing element, whereas the second type of straps is selectively located for firmly securing the wrap to the body portion, for example during body movement. There typically are at least two sets of each type of strap, each at a different location along the width of the web element to be deployed at different axial locations on the body portion being treated. The strap elements preferably employ hook and loop type fasteners, on the straps and on the web element, for ready connection, adjustment, and release.

Another feature of the invention resides in a pliable pocket panel on the web element and which at least partly overlies the inner surface of the web element. The pocket panel has a first outside dimension which is longitudinal with the length dimension of the web element and a second outside dimension which is longitudinal with the width dimension of the web element.

A portion of the web element which the pocket panel overlies is substantially free of restraint by the pocket panel from stretching along the length direction. This portion of the web element preferably extends for at least the full span of the pocket panel in the second dimension, and for at least part of the first dimension. To this end, the pocket panel has a portion which overlies the web panel portion and yet is substantially free of restraint on the lengthwise stretch of the web element.

In the illustrated preferred embodiment, the pocket panel has an overlap portion which is free of stretch-restraining connection with this stretchable portion of the web element. More particularly, this pocket panel has a seating portion secured, as by stretching, to the web element along a first path by form with the web element a re-entrant pocket. The pocket bottom is spaced distally from the pocket opening along the length dimension. The first path extends at least along part of the second outside dimension and along only a portion of the first outside dimension. The pocket panel also features an overlap portion which extends at least in the length dimension from the pocket opening and away from the pocket bottom for the remainder of the first outside dimension. The web element is free of stitching or other attachment to the overlap portion, and hence is free to stretch longitudinally without restraint by that portion of the pocket panel.

The thermo-formable bracing element is removably and replaceably received between the pocket panel and web element with only a portion of the element seated in the pocket. The remaining portion is covered by the overlap portion of the pocket panel. Thermal insulation provided by the pocket panel, or by a further element, thermally insulates the inner surface of the web element from the heat of the bracing element, when it is heated for thermo-forming.

The invention also features an improved orthopedic support apparatus for a body portion which extends along an axis and has a pliable wrap with a pocket which receives a removable and replaceable thermo-formable bracing element. The features include an adjustable strap element extending longitudinally opposite to the direction in which the pocket opening faces. A portion of the web wrap which extends beyond the pocket opening, and a pocket flap, effect closure of the pocket opening upon lifting about the axis of the body portion.

The invention also includes a process for fitting an orthopedic device as described to a body portion. The process includes the feature whereby the device as described above with the pocket opening facing in the opposite direction from the straps is wrapped about the body portion. As the wrap extension beyond the pocket panel is lifted, the pocket opening closes. The other side of the wrap is then brought about the body portion in the opposite direction, so that the device circumferentially wraps about the body portion and is thereafter secured.

An orthopedic support according to the invention provides unusually well-fitting and comfortable support for small and irregularly-shaped body portions such as a hand, wrist and forearm, among others. The support can be fitted quickly, within minutes, and is remarkably light in weight.

The invention accordingly comprises an article of manufacture possessing the features, properties and the relation of elements exemplified in the article hereinafter described, and the process of applying such an article, and the claims indicate the scope of the invention.

BRIEF DESCRIPTION OF THE DRAWING

For a fuller understanding of the nature and objects of the invention, reference is made to the following detailed description and accompanying drawing, in which.

DESCRIPTION OF THE ILLUSTRATED EMBODIMENTS

The invention features orthopedic support apparatus and a method of fitting such apparatus to a body portion. The apparatus and method are particularly suitable for body portions having sharp and reverse curves and short radii of curvature. The apparatus employs a wrap with a pocket that seats a removable and replaceable panel.

Figure 1:
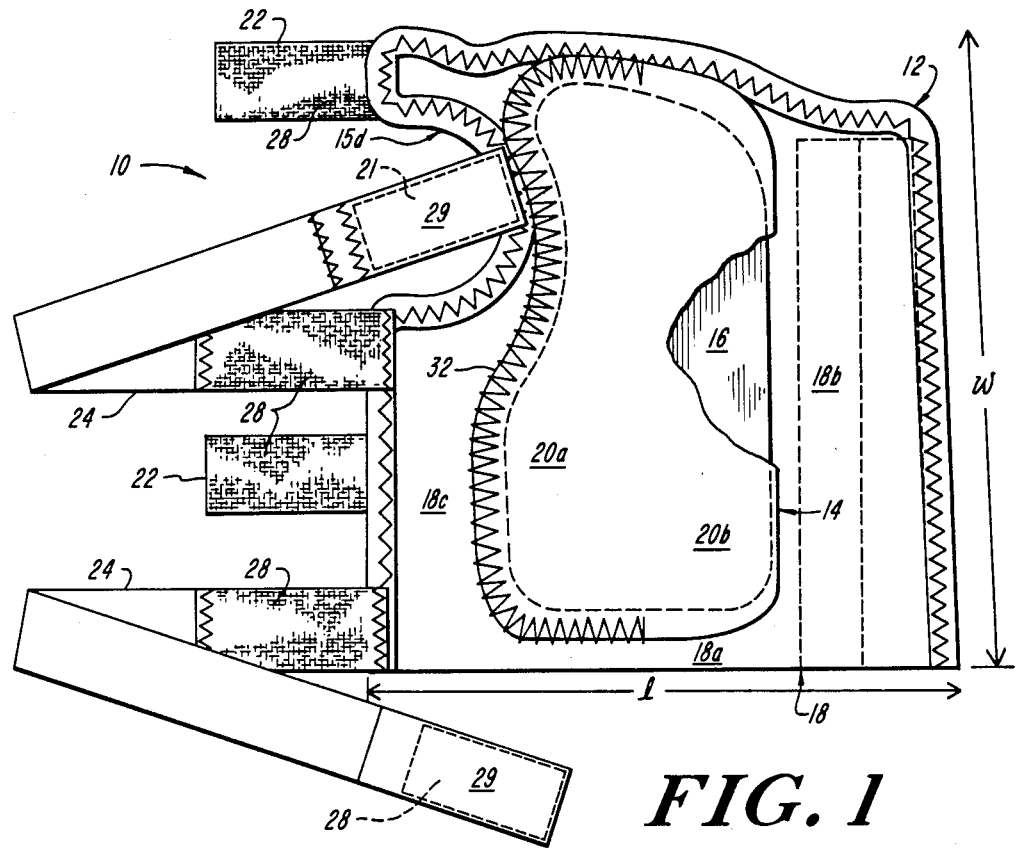
FIGS. 1 and 2 are inside and outside plan views, respectively, of an orthopedic wrist support device according to the invention.
Figure 2:
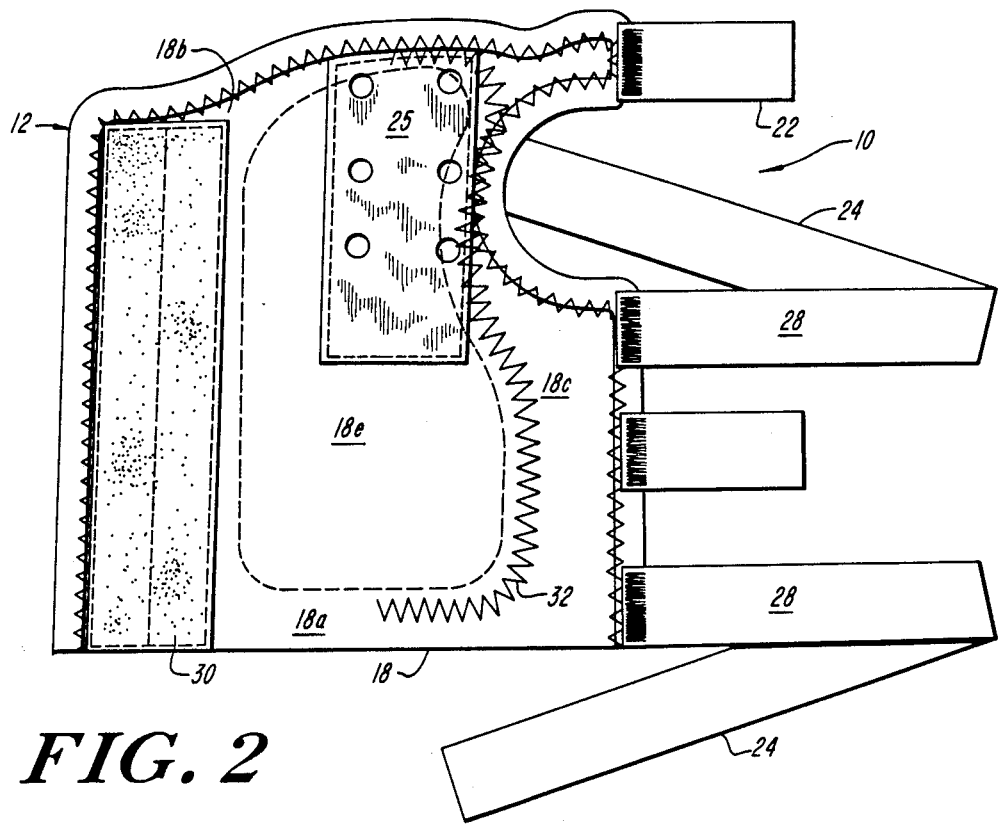

FIGS. 1 and 2 shows that an orthopedic device 10 according to the invention for a small body portion and particularly adapted for the right wrist has a pliable wrap 12 that has a pocket 14 on the inner side and in which is seated a thermo-formable bracing element 16.

Figure 3:
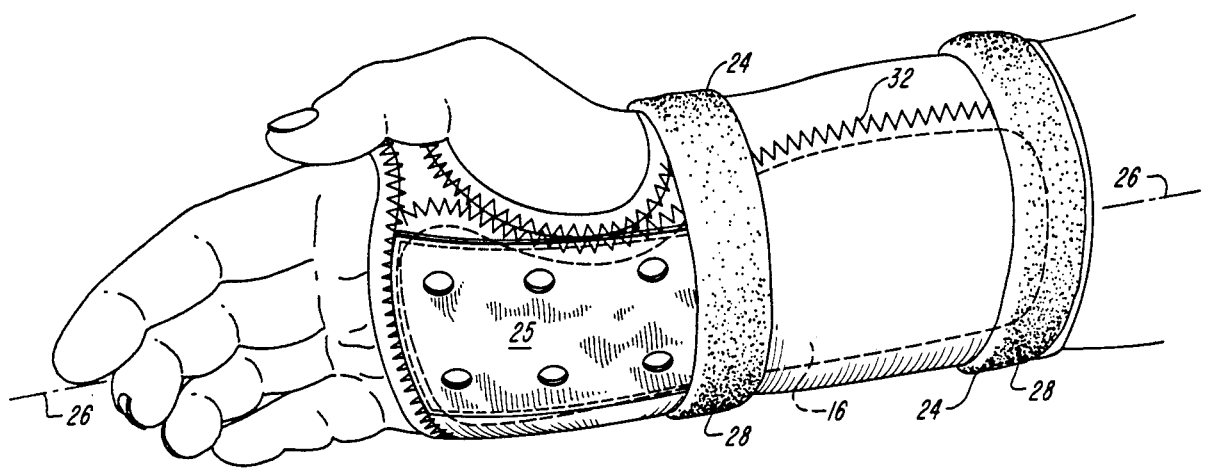
FIG. 3 shows the wrist device of FIGS. 1 and 2 fitted to a patient.
Figure 3A:
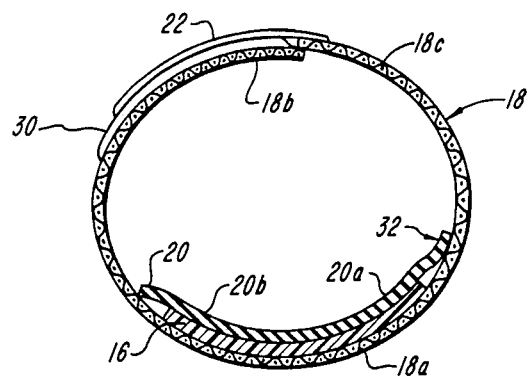
FIG. 3A is a simplified cross view.

The wrap 12 includes a web element 18, a pocket panel 20 (20a, 20b), securing strap elements 22 and supporting strap elements 24. The illustrated wrap fits on the right wrist of a subject, as shown in FIG. 3, with the web element 18 encircling the body portion, circumferentially about the longitudinal axis 26 of the body portion.

The web element 18 has a maximal length dimension, $l$, that extends circumferentially about the wrist. A preferred length, as illustrated, is sufficient for the web element to fully encircle the body portion being supported, with one lengthwise opposed edge overlapping the other. The web element has a maximal width dimension, $W$, that extends along the wrist axis 26, when the device 10 is fitted. The illustrated width dimension is sufficient to extend from forward of the thumb to at least a median section of the forearm.

With further reference to FIGS. 1 and 2, the web element is pliable and is elastic, to strech along at least the length dimension. The illustrated web element 18 is formed of a single piece of woven fabric. The illustrated device also has a pliable reinforcing pad 25, of leather or a like durable material, on the outer surface to cover the palm of a wearer, as appears in FIGS. 2 and 3, for protecting the device from wear when the user engages in manual activity.

The web element is configured with three portions arranged side-by-side along the length dimension, namely a central portion 18A, a first wrap portion 18B that extends from the side of the central portion adjacent the opening of pocket 14, and a second wrap portion 18C on the other side of the central portion. The central portion 18A of the web element is configured to overlay at least the base of the palm and the underside of the wrist when the device is in place, as appears in the detail of FIG. 3. The first wrap portion is configured to encircle part of the wrist and back of the hand about the side of the limb adjacent the small finger. It is sufficiently long to extend along the back of the limb to lie underneath the second warp portion 18C, which is configured to encircle about the other, thumb, side of the limb and to extend across the back of the limb to overlap the first wrap portion 18B.

As shown, the periphery of the web element 18 is configured to accomodate the right wrist, and particularly to allow the patient's thumb to protrude through an opening through the device when it is in place, as appears in FIG. 3. A prominent feature of this contour is a prominent truncated circular cutout 18d in the second wrap portion 18C of the web element 18, proximal to the forward end, through which the thumb passes when the device is in place.

As further shown in FIGS. 1 and 2, a first securing strap element 22 extends in the length direction from the web second wrap portion 18C adjacent to the front end of the device and a second securing strap element 22 is secured to the same portion spaced from the back of the device by approximately one-third of the width dimension. The two securing strap elements 22 are relatively short, preferably long enough to be grasped between two fingers and held taut for securing the wrap 12 encircled, with lengthwise tension, about a patient's wrist and lower palm. The illustrated device 10 includes hook and loop-type fasteners to secure the strap elements in place. As illustrated, the innerside of each securing strap element 22 includes a hook and loop fastener 28 which matingly engages a hook and loop fastening strip 30 that runs along the full width of the web first strap portion 18A, on the outer face of the device.

The illustrated device 10 has two supporting strap elements 24 each secured to the web second wrap portion 18C and extending in the lengthwise direction, as shown in FIGS. 1 and 2. One is located proximal to the back end of the device and the other is located proximal to the back end of the thumb cutout. These supporting strap elements 24, as illustrated in FIG. 3, are sufficiently long to encircle the wrist, or other body portion being supported, completely. Each illustrated supporting strap element 24 has a hook and loop fastener 28 at the base thereof, adjacent the web element 18, for engagement with the hook and loop fastening panel 30 when in place. It further has a wrist-encircling length extending therefrom for fully encircling the wrist so that the remote end, which carries a further hook and loop fastener on its inner face, overlaps the same strap and engages with a hook and loop fastener on the outer face, as appears in FIG. 3. The four illustrated strap elements, i.e. two securing strap elements 22 and two supporting strap elements 24 are preferably of woven fabric material and have little stretch or elasticity.

As further shown in FIG. 1, the pocket panel 20 on the inner side of the wrap 12 overlies the major portion of the web element 18 central portion 18A in both the length and width dimensions. The pocket panel is configured to receive and locate a bracing element 16 that has a width dimension approximately three times the length dimension thereof, for supportingly engaging the underside of a person's wrist, as FIG. 3 illustrates. The pocket panel is secured to the web element 18, suitably by stitching, for forming the pocket 14, along a path 32, which extends at least along part of the width dimension and along only a portion of the length dimension of the pocket panel. More particularly, the stitch path 32 in the illustrated device 10 extends along the entire width dimension of the pocket panel 20 and along only approximately one-half of the length dimension of the pocket panel. The stitch path 32 is continuous and thus extends, starting from the front end of the device, at approximately the midpoint of the web element in the length dimension and extends lengthwise to the left in FIG. 1, along the entire width dimension that is on the junction between the web element portions 18A and 18C, and then back along the length dimension, to the right in FIG. 1, for again approximately one-half of the length dimension of the pocket panel. This stitch path forms the pocket 14 with a pocket opening facing in the direction of the first web wrap portion 18B and a pocket bottom opposite thereto. Thus, the pocket opening faces along the longitudinal dimension and away from the direction in which the strap elements 22 and 24 extend from the web element 18C.

The pocket panel 20 is thus stitched or otherwise secured to the web element 18 along only a portion of the length dimension thereof. That is, it has a seating portion 20A that is secured along three peripheral sides to the web element 18 and has an overlap portion 20B that extends from the seating portion along the length dimension to the pocket opening. It is noteworthy that the overlap portion of the illustrated pocket panel is not stitched or otherwise secured to the web element 18.

This lack of stitching or other securage leaves the web element free to stretch lengthwise where it is overlapped by the pocket overlap portion 20B. That is, the web element 18 has a portion 18e which the pocket panel overlies and yet which is free of securage to the pocket panel along a panel overlap portion 20B adjacent the pocket opening. This freedom from securage enhances lengthwise stretching of the web element when it is applied to a patient. The enhanced stretch facilitates the thermo-forming of a heated bracing element seated in the pocket to the contour of the patient's body.

The overlap portion of the pocket panel typically extends widthwise along the entire width of the pocket panel and extends lengthwise along approximately half of the pocket panel length dimension. It is sufficiently large to completely cover the bracing element 16 seated in the pocket and thereby thermally shields the hot bracing element from the patient's skin. The overlap portion also cushions the entire extent of the bracing element from the wearer, for comfort.

The pocket panel 20 preferably is a compliant pliable sheet-like structure having a selected thermal resistance to shield the user's skin from a heated bracing element 16 in the pocket 14. One preferred material for the pocket panel is an open-cell polyether foam of having a thin woven fabric gauze, e.g. of nylon on both sides.

Figure 4:
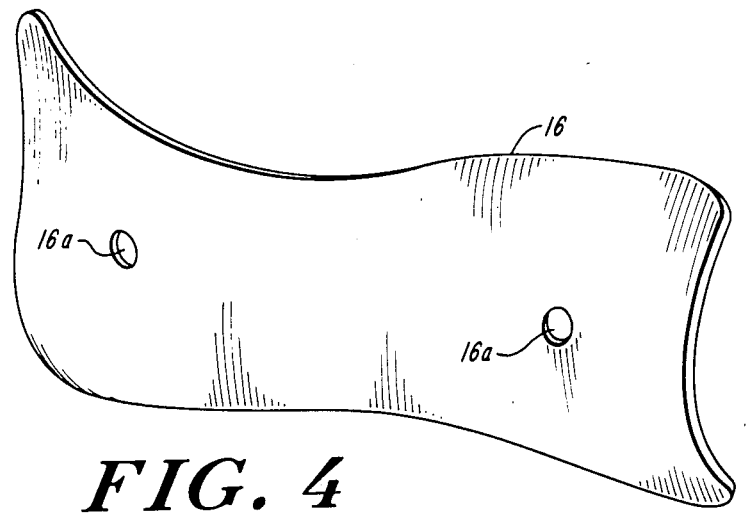
FIG. 4 shows a bracing element of the wrist device of FIG. 3 as molded to fit a patient.

The illustrated bracing element 16 is a thermo-formable panel of thermo-plastic material, preferably a synthetic copolymer as described further in U.S. Pat. No. 4,572,167 and as marketed by Rohm and Haas under the trade designation Kydex. As shown in FIG. 1, the illustrated bracing element 16 for a wrist orthosis has a width dimension approximately three times the length dimension and is contoured along one width-wise side to fit around and not overlap the base of a user's thumb. A preferred bracing element 16 is apertured with one or more through holes 16A, as appears in FIG. 4, to reduce weight and to reduce resistance to thermo-forming around complex contours. The materials for the device 10 can, by way of further illustrative example, be in accord with the description in the above-noted U.S. Pat. No. 4,572,167; and with the ORTHO-MOLD ® spinal orthosis device marketed by Ortho-Mold Bracing Systems of Boston, Mass..

A wrist support device 10 having the foregoing construction is used by heating the bracing element 16 by itself, i.e. removed from the wrap, as on a warming tray, to render it readily thermo-formable. The heated bracing element is inserted into the pocket 14 of the device. The wrap 12 with the bracing element seated in the pocket 14 is then placed against the lower palm and wrist underside of the subject, i.e. the central web portion 18A is positioned in contact with the patient. The web first wrap portion 18B is then folded to partially encircle the wrist. Next, the web second wrap portion 18C is folded around the other side of the wrist to further encircle the wrist and to overlap the first wrap portion 18B. The two wrap portions are pulled taut by the orthopedic practitioner, which tensions the web element 18 in the length dimension and accordingly subjects it to stretching in this direction. Each securing strap element 22 is pulled taut and secured to the velcro hook and loop panel 30 to secure the wrap 12 encircling the patient's wrist and under lengthwise tension.

Upon folding the web portion 18B to partially encircle one side of the patient's wrist, the pocket 14 is effectively closed, since the web portion 18B when thus disposed constricts the pocket opening. This pocket closing action prevents the bracing element 16 from being urged out of the pocket upon further fitting of the wrap to the patient.

Further, the lengthwise stretching of the web element 18 as it is fitted encircling the patient and secured in place with the securing straps 22 firmly urges the thermo-formable bracing element 16 against the contour of the patient's lower palm and wrist underside. The bracing element 16 accordingly readily thermoforms to fit the patient, as indicated in FIG. 3, and as further shown in FIG. 4. The medical practitioner typically gently presses on the outside of the wrap 12 over the bracing element 16 to enhance the molding of the bracing element exactly to the contour of the patient. The thermal insulation of the pocket panel 20 protects the patient from injury or discomfort due to the heat of the bracing panel. Further, the bracing panel quickly cools and hardens. The entire fitting process typically takes only one or two minutes, and the bracing element 16 typically is sufficiently cool to be firm and solid within three or four minutes after removal from the heating device.

The securing strap elements 22 thus are located and otherwise arranged to secure the device 10 to the wrist or other body portion quickly and with longitudinal tension in the web element 18 at locations relative to the patient's body portion which require a relatively high degree of forming of the brace element 16. This location and arrangement includes configuring the securing strap elements for directly interconnecting the longitudinally opposed ends of the web elements 18, i.e. the edges of the portions 18B and 18C. Further, it includes locating the securing strap elements 22 on the web element 18 for placement adjacent or proximal to shapes or contours on the patient's body portion which have small radii and/or reverses in curvature, as at the base of a palm as illustrated in FIG. 2.

The supporting strap elements 24 are located and otherwise arranged to secure the device 10 to the wrist for supporting and substantially immobilizing the wrist during varied movements and motions so as to provide superior orthosis for that body portion. This includes providing each supporting strap element with sufficient length to fully wrap around the body portion for secure and preferably stretch-free engagement with it. Further, it includes locating one supporting strap element 24, i.e. the forward one in FIG. 3, at the wrist joint, which is a point of maximal body flexure. A further supporting strap element 24, i.e. the rearward one in FIG. 3, is located at a point on the patient's body portion that undergoes relatively little flexure or minimal, to provide a secure stable anchorage of the device 10 to the supported body portion, with relatively little movement.

Figure 5:
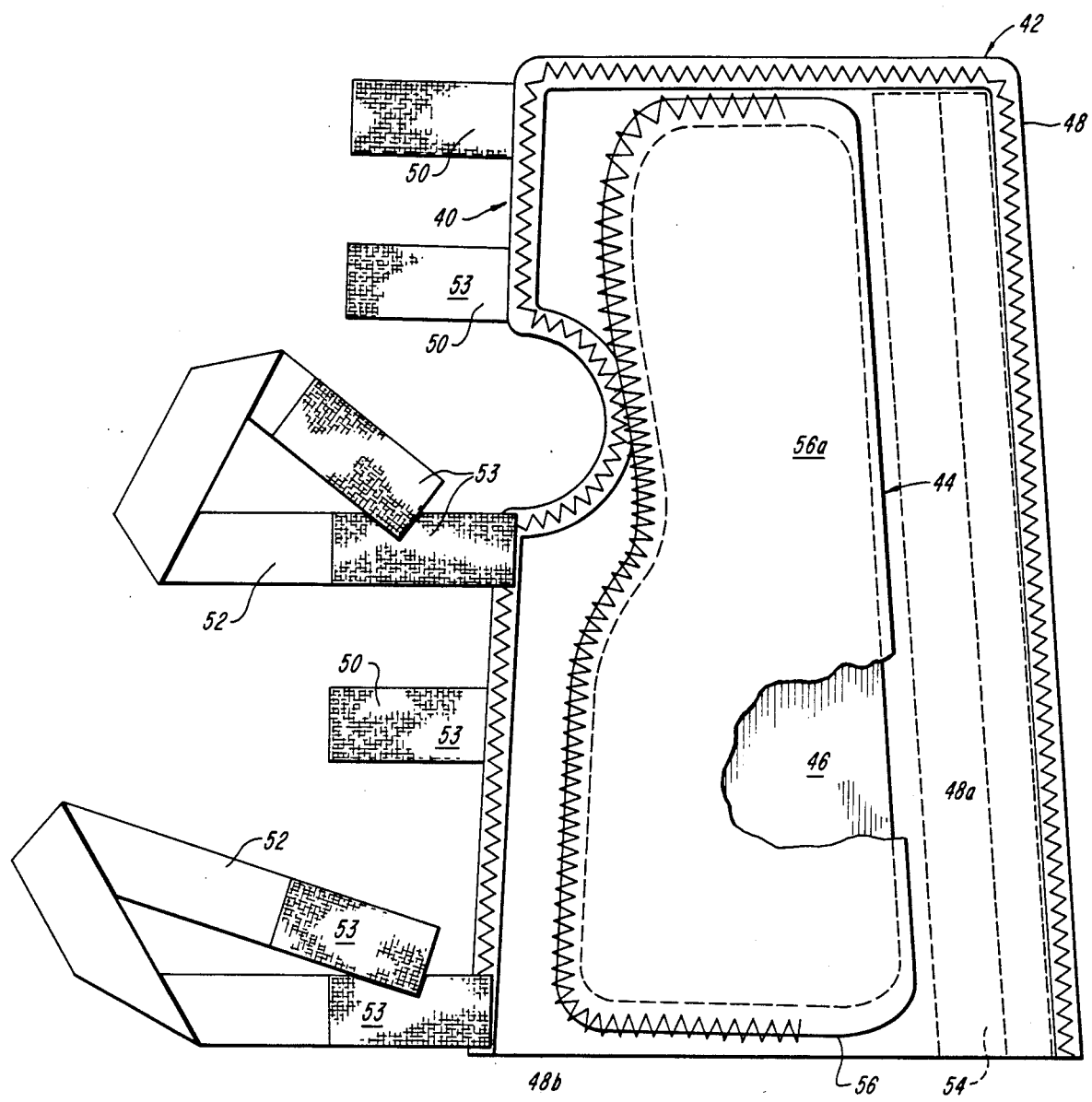
FIG. 5 is a plan view of another orthopedic device according to the invention.
Figure 6:
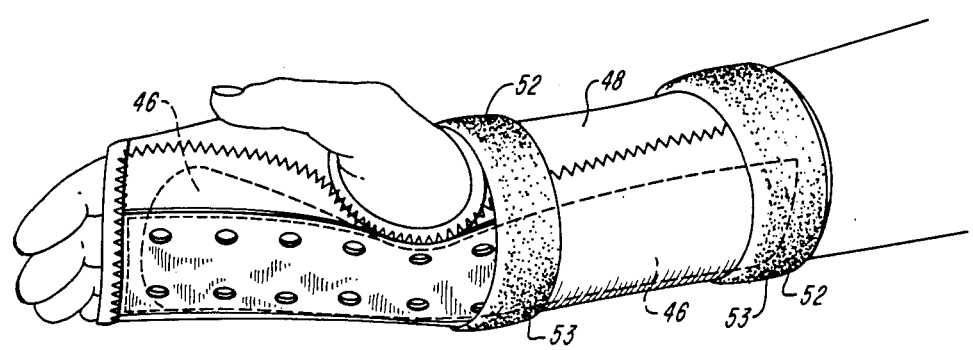
FIGS. 6 and 7 show the device of FIG. 4 fitted as a hand wrist orthosis, and as a dorsal extension control orthosis, respectively.
Figure 7:
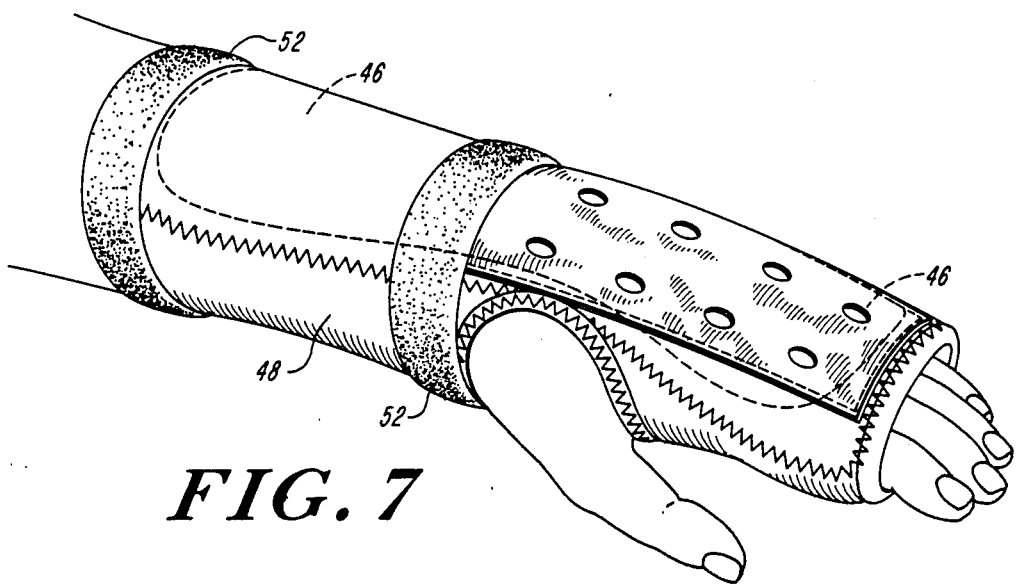

FIG. 5 shows another orthopedic device 40 according to the invention and which provides combined hand and wrist orthosis and, on the opposite hand, provides dorsal extension control orthosis, as shown in FIGS. 6 and 7, respectively. The support device 40 has a structure similar to that of device 10 described above. It accordingly has a wrap 42 which carries on its inner surface a pocket 44 that seats a thermo-formable bracing element 46. The wrap 42 is formed with a web element 48 to which are fastened securing straps 50 and support straps 52. The straps are fitted with hook and loop fastening strips 53, and the outside edge of the web element 48, opposite to where the straps are secured, carries a hook and loop fastening panel 54. A pocket panel 56 is secured along part only of its periphery to the web element and hence has a stretch-enhancing overlap portion 56A.

The web element 48 is configured as in FIGS. 1 and 2 to support the base of the hand and the wrist and is further elongated to support at the forward edge the interphalangal joint and, at the other end, to provide additional forearm support. The illustrated device 40 employs two securing straps 50 on the frontal extension that provides interphalangal joint orthosis, and a further such strap along the forearm. In addition, the device as illustrated has two support straps 52, one proximal to the wrist joint when the device is in place, and the other distal thereto along the forearm.

As with the device 10 described above, the device 40 of FIG. 5 is formed with the bracing element pocket 44 having an opening facing in the direction opposite to the attachment of the straps 52 and 54 to the web element. It further has a web element portion 48A which extends in the lengthwise direction beyond the central web portion 48B for commencing the first wrap step about a patient's forearm and hand, and for thereby constricting the pocket opening to prevent dislodgement of the bracing element seated therein.

FIG. 6 illustrates the support device 40 applied to a right hand to provide combined wrist and hand orthosis. In particular, it provides a volar flexion control orthosis with an extension to the proximal interphalangal joint and yet with a high degree of thumb mobility. The provision of the pocket panel overlap portion 56A enhances longitudinal stretch of the web element 48 about the varying contours of the patient's hand and thereby enhances the thermo-forming molding of the bracing element upon initial application to the patient.

FIG. 7 shows the same support device 40 as applied to a dorsal extension control orthosis on the opposite, left hand. In this application, the bracing element is on the back of the hand. For either placement, as is shown in FIG. 6 or in FIG. 7, the support device 40 provides ready and accurate thermo-forming of the bracing element to the patient.

Alternatives to the foregoing construction features of the invention can be practiced by employing a pocket panel that readily stretches in the lengthwise direction and by employing stretch-accomodating stitching or other sewage of the pocket panel to the web element. Also, the pocket panel can be a compliant fabric or like member which seats and thereby positions the bracing element, without providing thermal insulation. A separate insulating element can then be provided, either secured in the pocket or removable from it, for removal after the bracing element is formed and cools. Further, the insulating element can be separate and insertable into the pocket, either together with the bracing element or separately. These and other variations on the device illustrated may have certain advantages. The illustrated construction is generally deemed preferable for reasons of simplicity in use and in patient safety and comfort.

Figure 8:
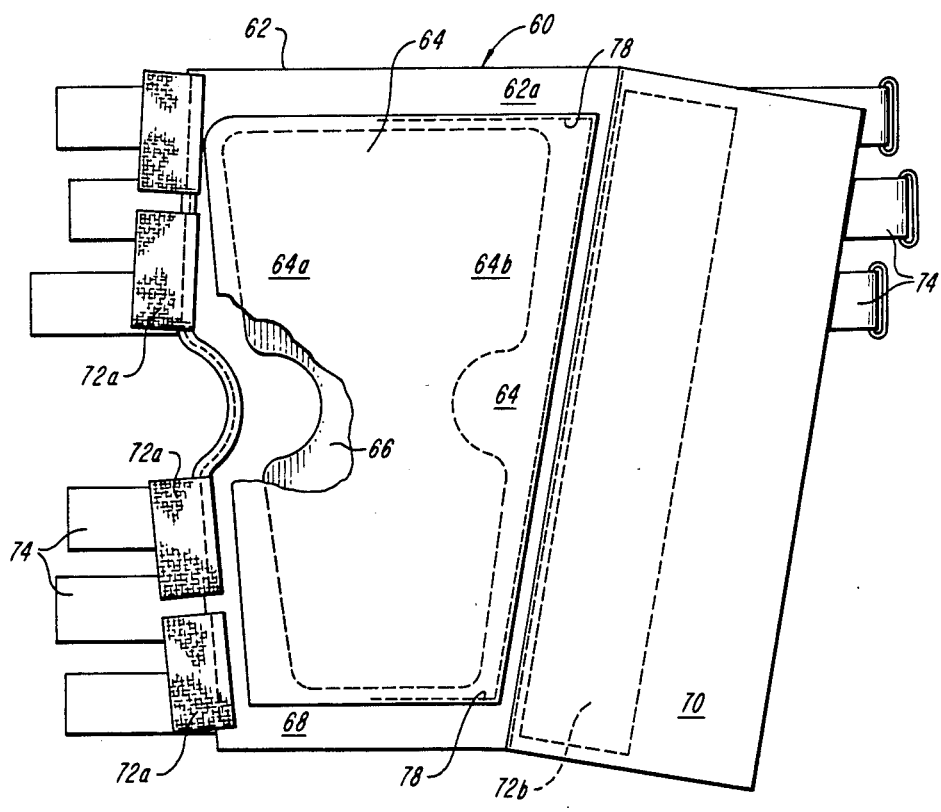
FIGS. 8 and 9 are inside and outside plan views, respectively, of an orthopedic knee support device according to the invention.
Figure 9:
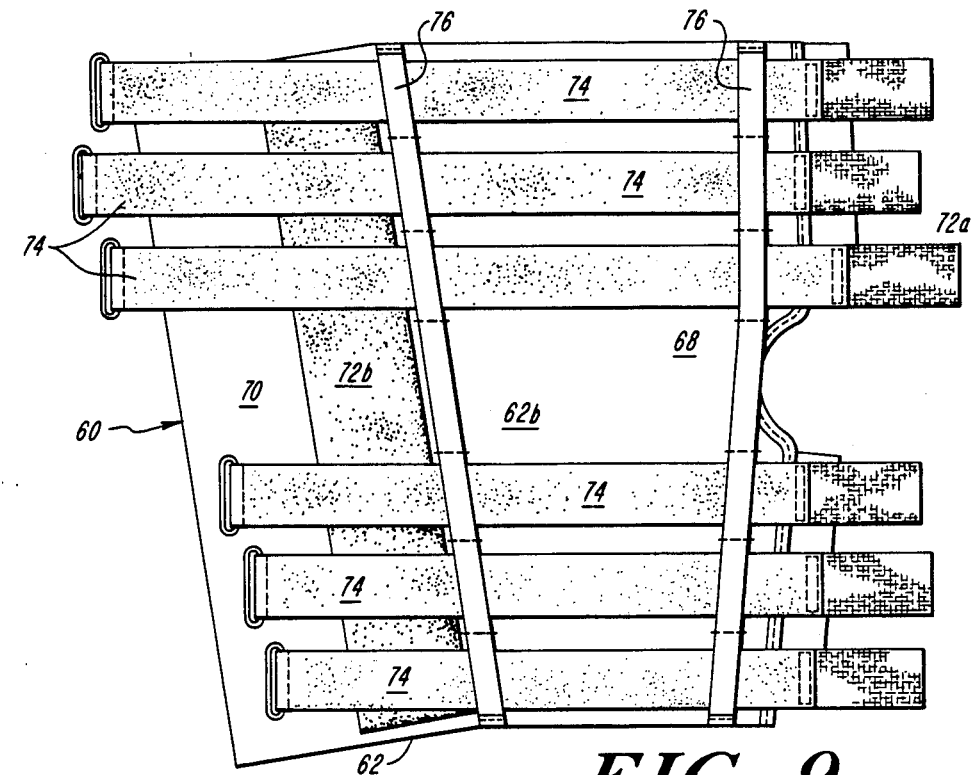

A knee support device 60 according to the invention has, as shown in FIGS. 8 and 9, a pliable wrap 62 that has a pocket panel 64 on the inner surface 62a and which removably and replaceably seats a bracing element 66.

The illustrating wrap 62 has an outer panel 68 that overlaps part of an under panel 70. The wrap encircles a patient's leg at the knee and at the portions above and below, i.e. at the femur section and the tibial section, as appears in FIG. 10 The outer panel is centered on the front of the leg and overlaps, typically at the side of the leg, the under panel which in turn spans the back of the patient's leg. A paired set of hook and loop fasteners 72, with one element 72a on the inner surface of the wrap at one longitudinal side of the outer panel and with another element 72b on the outer surface at the other longitudinal side, overlap and engage when the device is fitted. This securage, which includes fastener elements 72 above the knee, along the femur section, and below the knee, along the tibial section, is engaged first, before strap elements 74.

The wrap outer panel 68 is of pliable fabric or like sheet material which is stretchable in the longitudinal direction, i.e. from left to right in FIGS. 8 and 9, and may also be stretchable in the width dimension. The under panel 70 may be part of the same element that forms the wrap outer panel, or may be a separate element joined to the former. A preferred structure for the knee device 60 employs an under panel 70 which is compliant and of absorbant cushioning material for enhanced patient comfort.

Figure 10:
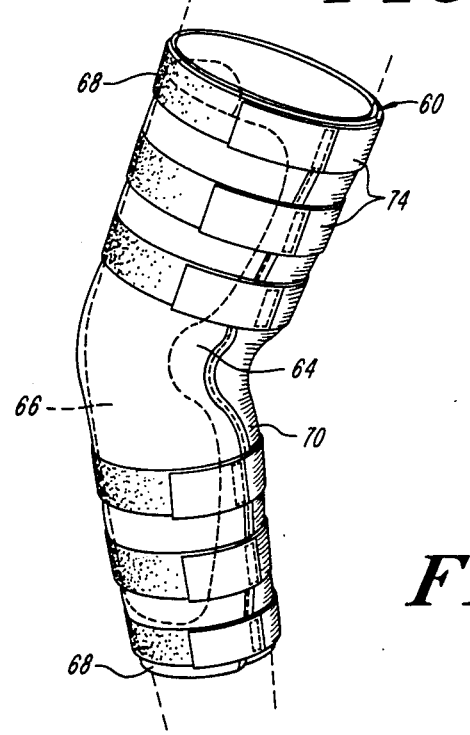
FIG. 10 shows the device of FIGS. 8 and 9 fitted to a patient.

The other set of strap elements 74 of the illustrated knee device 60 employs straps arranged for encircling the patient's leg both above and below the knee joint, as FIG. 10 shows. In particular, the illustrated plurality of strap elements 74 are secured with looped straps 76 to the wrap outer panel 68 and extend substantially parallel to the longitudinal direction, as appears in FIG. 9. Each illustrated strap element 74 includes inter-engageable hook and loop fasteners for securing opposite ends of the straps together. The illustrated straps employ a cinch ring at one end through which the other strap end passes before engaging the hook and loop fasteners. The strap elements 74 preferably have little, if any, elasticity.

With further reference to FIGS. 8 and 10, the pocket panel 64 overlies a major portion of the wrap outer panel 68, to support and cover a brace element 66, and can extend lengthwise around at least one third of the leg circumference, centered in front over the knee. The pocket panel extends in width, i.e. vertically in FIGS. 8–10, to accommodate a one-piece brace element that extends from well up on the femur section to well down on the leg tibial section. This extensive span of the brace element, both vertically on either side of the knee joint and circumferentially around the sides of the knee joint, provides strong, secure and reliable support. Moreover, the brace device of the inventio nenables the brace element 66 to conform closely to the leg structure of each individual patient.

The illustrated brace element 66 has a frusto-wedge shape, as appears in FIG. 8, with smallest dimension in the length direction at the bottom and with the largest span in the length direction at the top. The illustrated brace element has a narrow bridging median neck, which seats at the knee joint, for accommodating thermo-forming with a bend in the patient's leg, as FIG. 10 illustrates.

The pocket panel 64 is secured, e.g. by stitching, to the wrap 62, and illustratively to the outer panel 68, along only a portion of the length dimension, to leave an overlap portion 64a of substantial lengthwise span free of securage to the wrap, other than by way of the stiched support portion 64b. In particular, as shown in FIG. 8 the securage of the illustrated pocket panel 64 is along a stitch path 78 that extends lengthwise along only substantially one-half the pocket panel length at the top and at the bottom, in addition to extending along the entire width on the panel side proximal to the under panel 70. Accordingly, a portion of the pocket panel 64, illustrated as approximately one-half, forms the overlap portion 64a. The underlying span of the wrap 62 is accordingly free to stretch longitudinally without restraint due to securage to the pocket panel 64.

As described above with reference to the wrist embodiments of the invention, the brace element 66 is of thermo-formable material and provision is made for thermal-insulation by the pocket panel 64 or otherwise between the brace element 66 when inserted in the pocket panel and the patient, to shield the patient from the elevated thermo-forming temperatures to which the brace element is heated for thermo-forming. One preferred practice is to employ a pocket panel 64 which includes a thermal barrier and which has a soft inner surface selected for patent comfort, even during prolonged contact with the patiet's body.

It will thus be seen that the object set forth above, among those made apparent from the preceding description, are efficiently attained. Since certain changes may be made in carrying out the above method and in the foregoing article without departing from the scope of the invention, all matter contained in the above description or shown in the accompanying drawing shall be interpreted as illustrative, and not in a limiting sense.

Having described the invention, what is claimed as new and secured by Letters Patent:

1. Orthopedic support apparatus for a body portion which extends along a first axis, said support apparatus having a pliable wrap with an inner surface, a length dimension and a width dimension, and which includes compliant web means resiliently elastic at least along said length dimension, said wrap further having adjustable strap means extending along said length dimension and adapted for securing said web means at least partially encircling the body portion about said axis with the length dimension extending circumferentially of the body portion and with said inner surface facing toward the body portion, said apparatus having the improvement comprising A. compliant pocket panel means on said wrap overlying said inner surface of said web means and having selected thermal insulation, said pocket panel means (1) having a first dimension longitudinal with said length dimension and a second dimension longitudinal with said width dimension, (2) having a seating portion secured to said web means along a first path to form with said web means a re-entrant pocket having a pocket bottom distal along said length dimension from a pocket opening, said first path extending along at least part of said second dimension and along only a portion of said first dimension, and (3) having an overlap portion extending at least in said length dimension from said seating portion away from said pocket bottom for the remainder of said first dimension, and B. a thermo-formable bracing element removably and replaceably received in said pocket between said pocket panel means and said web means and having a portion thereof seated by said seating portion and having the remaining portion thereof covered by said overlap portion, C. and wherein said web means is free of securage to said pocket panel means at said overlap portion so that said web means is free to stretch at least along said length direction without restraint by pocket-forming securage to said overlap portion.

2. Orthopedic apparatus according to claim 1 having means including stitching providing securage of said seating portion to said web means.

3. Orthopedic support apparatus according to claim 1 wherein said strap means comprises a first set of straps and a second set of straps, said first set of straps being adapted for initial securage of said wrap about the body portion with said wrap tensioned along said length dimension thereof, and said second set of straps being adapted for substantially immobilized securage of said wrap about the body portion.

4. Orthopedic support apparatus according to claim 1 having the further improvement in which A. said web means has first, second and third portions arranged side by side along said length dimension with said strap means being secured to said third portion and with said pocket panel means overlying said second portion and, further, with said pocket opening facing toward said first portion, and wherein said first portion effects closure of said pocket opening upon being wrapped about the body portion.

5. Orthopedic support apparatus for a body portion which extends along a first axis, said support apparatus having a pliable wrap with an inner surface, a length dimension and a width dimension, and which includes compliant web means resiliently elastic at least along said length dimension, said wrap further having adjustable strap means extending along said length dimension and adapted for securing said web means at least partially encircling the body portion about said axis with the length dimension extending circumferentially of the body portion and with said inner surface facing toward the body portion, said apparatus having the improvement comprising A. compliant pocket panel means on said wrap overlying said inner surface of said web means, said pocket panel means
    (1) having a first dimension longitudinal with said length dimension and a second dimension longitudinal with said width dimension,
    (2) having a seating portion secured to said web means along a first path to form with said web means a re-entrant pocket having a pocket bottom distal along said length dimension from a pocket opening, said first path extending along at least part of said second dimension and along at least part of said first dimension, B. a thermo-formable bracing element removably and replaceably received in said pocket between said pocket panel means and said web means with at least a portion thereof seated by said seating portion, C. means for thermally insulating said wrap inner surface from heat of said bracing element received in said pocket, and D. a portion of said web means which said pocket panel means overlies being substantially free of restraint by said pocket panel means from stretch along said length direction, said web means portion extending at least the full span of said second dimension and at least part of said first dimension.

6. Orthopedic support apparatus according to claim 5 wherein said pocket panel means has an overlap portion extending in said length dimension from said seating portion away from said pocket bottom and which is substantially free of stretch-restraining connection with said web means.

7. Orthopedic support apparatus for a body portion which extends along a first axis, said support apparatus having a pliable wrap with an inner surface, a length dimension and a width dimension, and which includes compliant web means resiliently elastic at least along said length dimension, said wrap further having adjustable strap means extending along said length dimension and adapted for securing said web means at least partially encircling the body portion about said axis with the length dimension extending circumferentially of the body portion and with said inner surface facing toward the body portion, said apparatus having the improvement comprising A. compliant pocket panel means on said wrap overlying said inner surface of said web means, said pocket panel means
    (1) having a first dimension longitudinal with said length dimension and a second dimension longitudinal with said width dimension,
    (2) having a seating portion secured to said web means along a first path to form with said web means a re-entrant pocket having a pocket bottom distal along said length dimension from a pocket opening, said first path extending along at least part of said second dimension and along at least part of said first dimension, B. a thermo-formable bracing element removably and replaceably received in said pocket between said pocket panel means and said web means with at least a portion thereof seatede by said seating portion, C. means for thermally insulating said wrap inner surface from heat of said bracing element received in said pocket, and D. a further portion of said pocket panel means overlying a portion of said web means along at least the full span of said second dimension and along at least part of said first dimension and being substantially free of restraint to stretch of said web means portion along said length dimension.

* * * * *

UNITED STATES PATENT AND TRADEMARK OFFICE
CERTIFICATE OF CORRECTION

PATENT NO. : 4,716,892
DATED : January 5, 1988
INVENTOR(S) : Sumner Brunswick

It is certified that error appears in the above-identified patent and that said Letters Patent is hereby corrected as shown below:

At Column 1, line 12, delete "iscloses", and insert --discloses--.

At Column 1, line 56, delete "boy", and insert --body--.

At Column 4, line 17, delete "20 (20a, 20b)", and insert --20,--.

At Column 7, line 48, delete "FIG. 2.", and insert --FIG. 3.--.

At Column 9, line 12, delete "FIG. 10", and insert --FIG. 10.--.

At Column 9, line 60, delete "inventio nenables", and insert --invention enables--.

Signed and Sealed this

Fourteenth Day of March, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,716,892

DATED : 5 January 1988

INVENTOR(S) : Sumner Brunswick

It is certified that error appears in the above-identified patent and that said Letters Patent is hereby corrected as shown below:

At column 4, line 45, delete "18A", and insert --18a--.

At column 4, line 45, delete "18B", and insert --18b--.

At column 4, line 48, delete "18C", and insert --18c--.

At column 4, line 49, delete "18A", and insert --18a--.

At column 4, line 56, delete "18C", and insert --18c--.

At column 4, line 59, delete "18B", and insert --18b--.

At column 4, line 66, delete "18C", and insert --18c--.

At column 5, line 3, delete "18C", and insert --18c--.

UNITED STATES PATENT AND TRADEMARK OFFICE
CERTIFICATE OF CORRECTION

PATENT NO. : 4,716,892

DATED : 5 January 1988

INVENTOR(S) : Sumner Brunswick

It is certified that error appears in the above-identified patent and that said Letters Patent is hereby corrected as shown below:

At column 5, line 17, delete "18A", and insert —18a—.

At column 5, line 21, delete "18C", and insert —18c—.

At column 5, line 42, delete "18A", and insert —18a—.

At column 5, line 61, delete "18A", and insert —18a—.

At column 5, line 62, delete "18C", and insert —18c—.

At column 5, line 66, delete "18B", and insert —18b—.

At column 6, line 2, delete "18C", and insert —18c—.

At column 6, line 6, delete "20A", and insert —20a—.

At column 6, line 7, delete "20B", and insert —20b—.

At column 6, line 14, delete "20B", and insert —20b—.

At column 6, line 17, delete "20B", and insert —20b—.

At column 6, line 49, delete "16A", and insert —16a—.

At column 6, line 65, delete "18A", and insert —18a—.

At column 6, line 66, delete "18B", and insert —18b—.

At column 6, line 68, delete "18C", and insert —18c—.

UNITED STATES PATENT AND TRADEMARK OFFICE
CERTIFICATE OF CORRECTION

PATENT NO. : 4,716,892

DATED : 5 January 1988

INVENTOR(S) : Sumner Brunswick

It is certified that error appears in the above-identified patent and that said Letters Patent is hereby corrected as shown below:

At column 7, line 2, delete "18B", and insert --18b--.

At column 7, line 9, delete "18B", and insert --18b--.

At column 7, line 11, delete "18B", and insert --18b--.

At column 7, line 43, delete "18B", and insert --18b--.

At column 7, line 43, delete "18C", and insert --18c--.

At column 8, line 14, delete "56A", and insert --56a--.

At column 8, line 30, delete "48A", and insert --48a--.

At column 8, line 32, delete "48B", and insert --48b--.

At column 8, line 41, delete "56A", and insert --56a--.

Signed and Sealed this

Twenty-fifth Day of July, 1989

Attest:

DONALD J. QUIGG

Attesting Officer

Commissioner of Patents and Trademarks